United States Patent
Mork et al.

(10) Patent No.: US 6,303,834 B1
(45) Date of Patent: Oct. 16, 2001

(54) HIGH INTERNAL PHASE EMULSIONS (HIPES) AND FOAMS MADE THEREFROM

(75) Inventors: Steven W. Mork; Gene D. Rose; Daniel Patrick Green, all of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/645,837

(22) Filed: Aug. 25, 2000

Related U.S. Application Data

(63) Continuation of application No. 09/195,273, filed on Nov. 18, 1998, now Pat. No. 6,147,131, and a continuation-in-part of application No. PCT/US98/07586, filed on Apr. 17, 1998, which is a continuation-in-part of application No. 08/558,333, filed on Nov. 15, 1995, now Pat. No. 5,977,194.
(60) Provisional application No. 60/046,910, filed on May 16, 1997.

(51) Int. Cl.$^7$ .................................................... C07C 43/20
(52) U.S. Cl. ............................................................ 568/614
(58) Field of Search .............................. 568/614; 558/34, 558/51

(56) References Cited

U.S. PATENT DOCUMENTS

| | | | |
|---|---|---|---|
| Re. 27,444 | 7/1972 | Will ....................................... | 260/2.5 |
| 3,244,772 | 4/1966 | von Bonin et al. . | |
| 3,343,599 | 9/1967 | Eddins, Jr. et al. . | |
| 3,352,109 | 11/1967 | Lissant ................................... | 60/217 |
| 3,378,418 | 4/1968 | Lissant . | |
| 3,396,537 | 8/1968 | Lissant et al. . | |
| 3,423,826 | 1/1969 | Liska . | |
| 3,490,237 | 1/1970 | Lissant . | |
| 3,539,406 | 11/1970 | Lissant . | |
| 3,613,372 | 10/1971 | Lissant . | |
| 3,617,095 | 11/1971 | Lissant . | |
| 3,734,867 | 5/1973 | Will ................................. | 260/2.5 R |
| 3,886,107 | 5/1975 | Najvar . | |
| 3,892,881 | 7/1975 | Lissant . | |
| 3,974,116 | 8/1976 | Lissant . | |
| 3,983,213 | 9/1976 | Lissant . | |
| 3,984,334 | 10/1976 | Hopper . | |
| 3,988,508 | 10/1976 | Lissant ................................... | 526/344 |
| 4,018,426 | 4/1977 | Mertz et al. . | |
| 4,037,665 | 7/1977 | Hopper . | |
| 4,168,239 | 9/1979 | Mertz et al. ............................. | 252/2 |
| 4,259,215 | 3/1981 | Murata et al. ........................ | 252/528 |
| 4,473,611 | 9/1984 | Haq ....................................... | 428/198 |
| 4,522,953 | 6/1985 | Barby et al. ........................... | 521/64 |
| 4,536,521 | 8/1985 | Haq ....................................... | 521/146 |
| 4,538,000 | 8/1985 | Parr ....................................... | 568/616 |
| 4,603,069 | 7/1986 | Haq et al. . | |
| 4,606,913 | 8/1986 | Aronson et al. . | |
| 4,606,958 | 8/1986 | Haq et al. . | |
| 4,608,197 | 8/1986 | Kesling, Jr. et al. . | |
| 4,611,014 | 9/1986 | Jomes et al. .......................... | 521/146 |
| 4,612,334 | 9/1986 | Jones et al. ........................... | 521/146 |
| 4,659,564 | 4/1987 | Cox et al. .............................. | 424/65 |
| 4,668,709 | 5/1987 | Jones et al. ........................... | 521/146 |
| 4,745,154 | 5/1988 | Ruffner ................................. | 524/801 |
| 4,746,460 | 5/1988 | Taylor ................................... | 252/314 |
| 4,775,655 | 10/1988 | Edwards et al. ..................... | 502/416 |
| 4,788,225 | 11/1988 | Edwards et al. ..................... | 521/147 |
| 4,797,310 | 1/1989 | Barby et al. . | |
| 4,889,885 | 12/1989 | Usuki et al. . | |

(List continued on next page.)

FOREIGN PATENT DOCUMENTS

| | | |
|---|---|---|
| 2145030 | 9/1996 | (CA) . |
| 0 068 830 | 1/1983 | (EP) . |
| 0 130 764 | 1/1985 | (EP) . |
| 0 060 138 | 9/1986 | (EP) . |
| 0 200 528 | 11/1986 | (EP) . |
| 0 297 179 | 1/1989 | (EP) . |
| 1 458 203 | 12/1976 | (GB) . |
| 2 054 635 | 2/1981 | (GB) . |
| 2 131 430 | 6/1984 | (GB) . |
| WO89/12618 | 12/1989 | (WO) . |
| WO93/04092 | 3/1993 | (WO) . |
| WO93/04113 | 3/1993 | (WO) . |
| WO94/13704 | 6/1994 | (WO) . |
| WO96/21474 | 7/1996 | (WO) . |
| WO96/40823 | 12/1996 | (WO) . |
| WO97/07832 | 3/1997 | (WO) . |
| WO97/18246 | 5/1997 | (WO) . |
| WO97/19129 | 5/1997 | (WO) . |
| 97/37745 | 10/1997 | (WO) . |
| 97/45456 | 12/1997 | (WO) . |
| 97/45479 | 12/1997 | (WO) . |

OTHER PUBLICATIONS

"High Internal Phase Emulsions and Porous Materials Prepared Therefrom", filed in the United States of America on Jun. 16, 1998, Application Ser. No. 09/098,259; Applicant: Steven W. Mork et al.

(List continued on next page.)

*Primary Examiner*—John M. Cooney, Jr.
(74) *Attorney, Agent, or Firm*—Edward W. Black

(57) ABSTRACT

High internal phase emulsions (HIPEs), porous polymeric materials made therefrom, and methods for making and using the same. Specific embodiments of the invention include water-in-oil high internal phase emulsions having at least 70 volume percent of an internal aqueous phase and less than 30 volume percent of an external oil phase wherein the oil phase comprises a vinyl polymerizable monomer and a surfactant effective to stabilize the emulsion. The subject surfactants are oil soluble and preferably include an oxyalkylene component.

9 Claims, No Drawings

U.S. PATENT DOCUMENTS

| | | | |
|---|---|---|---|
| 4,965,100 | 10/1990 | Leigh et al. | 427/242 |
| 4,965,289 | 10/1990 | Sherrington et al. | 521/53 |
| 4,985,468 | 1/1991 | Elmes et al. | 521/63 |
| 5,001,165 * | 3/1991 | Canaday et al. | 252/182.27 |
| 5,006,339 | 4/1991 | Bargery et al. | 424/404 |
| 5,021,462 | 6/1991 | Elmes et al. | 521/63 |
| 5,147,345 | 9/1992 | Young et al. | 604/378 |
| 5,149,720 | 9/1992 | DesMarais et al. | 521/63 |
| 5,150,576 | 9/1992 | Minzenberger | 62/11 |
| 5,162,475 | 11/1992 | Tang et al. | 526/333 |
| 5,187,070 | 2/1993 | Fung et al. | 435/25 |
| 5,198,472 | 3/1993 | DesMarais et al. | 521/63 |
| 5,200,433 | 4/1993 | Beshouri | 521/64 |
| 5,210,104 | 5/1993 | Bass et al. | 521/64 |
| 5,250,576 | 10/1993 | DesMarais et al. | 521/63 |
| 5,252,619 | 10/1993 | Brownscombe et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,292,777 | 3/1994 | DesMarais et al. | 521/64 |
| 5,296,627 * | 3/1994 | Tang et al. | 568/614 |
| 5,306,734 | 4/1994 | Bass et al. | 521/63 |
| 5,318,554 | 6/1994 | Young et al. | 604/378 |
| 5,324,862 | 6/1994 | Yokota et al. | 568/608 |
| 5,331,015 | 7/1994 | DesMarais | 521/62 |
| 5,332,854 | 7/1994 | Yokota et al. | 558/33 |
| 5,334,621 | 8/1994 | Beshouri | 521/64 |
| 5,348,974 | 9/1994 | Wright et al. | 514/456 |
| 5,352,711 | 10/1994 | DesMarais | 521/149 |
| 5,358,974 | 10/1994 | Brownscombe et al. | 521/64 |
| 5,387,207 | 2/1995 | Dyer et al. | 604/369 |
| 5,397,316 | 3/1995 | LaVon et al. | 604/369 |
| 5,500,451 | 3/1996 | Goldman et al. | 521/64 |
| 5,550,167 | 8/1996 | DesMarais | 521/50 |
| 5,563,179 | 10/1996 | Stone et al. | 521/64 |
| 5,571,849 | 11/1996 | DesMarais | 521/64 |
| 5,632,737 | 5/1997 | Stone et al. | 604/358 |
| 5,633,291 | 5/1997 | Dyer et al. | 521/64 |
| 5,641,433 | 6/1997 | Chirinos et al. | 252/312 |
| 5,646,193 | 7/1997 | Brownscombe et al. | 521/63 |
| 5,649,920 | 7/1997 | Levon et al. | 604/385.2 |
| 5,650,222 | 7/1997 | DesMarais et al. | 442/370 |
| 5,652,194 | 7/1997 | Dyer et al. | 502/402 |
| 5,670,087 | 9/1997 | Chirinos et al. | 252/311.5 |
| 5,692,939 | 12/1997 | DesMarais | 442/373 |
| 5,728,743 | 3/1998 | Dyer et al. | 521/64 |
| 5,741,581 | 4/1998 | DesMarais et al. | 428/284 |
| 5,744,506 | 4/1998 | Goldman et al. | 521/64 |
| 5,753,359 | 5/1998 | Dyer et al. | 428/315.5 |
| 5,763,499 | 6/1998 | DesMarais | 521/64 |
| 5,767,168 | 6/1998 | Dyer et al. | 521/149 |
| 5,770,634 | 6/1998 | Dyer et al. | 521/64 |
| 5,786,395 | 7/1998 | Stone et al. | 521/64 |
| 5,795,921 | 8/1998 | Dyer et al. | 521/146 |
| 5,817,704 | 10/1998 | Shiveley et al. | 521/63 |
| 5,851,430 | 12/1998 | Chirinos et al. | 252/311.5 |
| 5,856,366 | 1/1999 | Shiveley et al. | 521/63 |
| 5,977,194 | 11/1999 | Mork et al. | 521/61 |

OTHER PUBLICATIONS

"High Internal Phase Emulsions and Porous Materials Prepared Therefrom", filed at the PCT on Apr. 17, 1998, International Application No. US/PCT98/07586, published as WO 98/51713 on Nov. 9, 1998, Applicant: Stephen W. Mork et al.

Reichle, Walter T., "Catalytic Reactions by Thermally Activated, Synthetic, Anionic Clay Minerals", *Journal of Catalysis*, vol. 94, pp. 547–557 (1985).

Lissant, "Making and Breaking Emulsions", Emulsion and Emulsion Technology Part 1, Chpt. 2, pp. 71–124 (1974).

Lewis, Hawley's Condensed Chemical Dictionary, $12^{th}$ Ed., p. 43 (1993).

Gmitter et al., "Flexible Polyurethane Foams", Plastic Foams, Part III, pp. 109–226 (1972).

Derwent Publications Ltd., JP 61 231 098 A, Kao Corporation (1988).

Yokota et al., "Synthesis of Polymerizable Surfactant and its Application to Emulsion Polymerization", Industrial Applications of Surfactants III, pp. 31–48 (1992).

Nagai, Katsutoshi, "Radical Polymerization and Potential Applications of Surface–active Monomers",*TRIP*, vol. 4, #4, Apr. 1996.

"High Internal Phase Emulsions (HIPEs) and Foams Made Therefrom", filed in the United States of America on Nov. 18, 1998, Application Ser. No. 09/195,273, Applicant: Stephen W. Mork et al.

"Multilayer Porous Polymeric Mateiral and Process for Preparing the Same," filed in the United States of America on Aug. 10, 1998, Application Ser. No. 09/131,307, Applicant: Steven W. Mork.

"Method for Treating Subterranean Formations," filed in the United States of America on Sep. 27, 1999, Application Ser. No. 09/406,860, Applicant: Gene R. Rose.

Williams et al., "Emulsion Stability and Rigid Foams from Styrene or Divinylbenzene Water–in–Oil Emulsions," *Langmuir*, vol. 6, pp. 437–444. (1990).

Williams et al., "Spatial Distribution of the Phases in Water–in–Oil Emulsions. Open and Closed Microcellular Foams from Crosslinked Polystyrene," *Langmuir*, vol. 4, pp. 656–662 (1988).

Yerges, "Sound, Noise, and Vibration Control," $2^{nd}$ Ed., Van Nostrand Reinhold Co., p. 59 (1978).

* cited by examiner

US 6,303,834 B1

HIGH INTERNAL PHASE EMULSIONS (HIPES) AND FOAMS MADE THEREFROM

RELATED APPLICATIONS

This application is a continuation of U.S. Ser. No. 09/195,273, filed Nov. 18, 1998 now U.S. Pat. No. 6,147,131, which is a continuation-in-part of: U.S. Ser. No. 08/558,333, filed Nov. 15, 1995 now U.S. Pat. No. 5,977,194, PCT/US 98/07586, filed Apr. 17, 1998, and U.S. Ser. No. 60/046,910, filed May 16, 1997, the contents of each of which are incorporated herein by reference.

BACKGROUND OF THE INVENTION

Water-in-oil emulsions are dispersions of discontinuous or discrete aqueous particles commonly referred to as the "internal" aqueous phase in a continuous or "external" oil phase. Emulsions can contain as much as and more than 70 volume percent internal phase. These are often referred to as high internal phase emulsions (HIPEs). The volume fraction of the internal aqueous phase in such emulsions can be as high as 90 percent and frequently is as high as 95 percent with some HIPEs being reported as high as 98 percent aqueous phase.

The use of high internal phase emulsions (HIPEs) in forming porous polymeric materials is well known. See for example: U.S. Pat. Nos. 5,210,104; 5,200,433; 4,536,521; 4,788,225; 5,147,345; 5,331,015; 5,260,345; 5,268,224 and 5,318,554. HIPE polymerization has gained increasing interest as open-celled polymeric foams having the capacity to absorb relatively high amounts of water and other liquids can be produced. In the described HIPEs, the external oil phase typically comprises a vinyl polymerizable monomer, such as 2-ethylhexyl acrylate and styrene, and a cross-linking monomer such as divinylbenzene. The internal aqueous phase typically comprises water, a radical initiator (if not in the oil phase) and an electrolyte. To form a stable emulsion, a HIPE surfactant is added to the oil phase prior to emulsification. Commonly used HIPE stabilizing surfactants include nonionic surfactants such as sorbitan esters (for example, sorbitan monooleate and sorbitan monolaurate). Other known HIPE stabilizing surfactants include certain polyglycerol aliphatic esters such as those described in U.S. Pat. No. 5,500,451 and 5,817,704, the entire contents of which are incorporated herein by reference.

In order to effectively stabilize HIPEs, the aforementioned surfactants must be used in relatively high concentrations (typically above 5 weight percent of the oil phase). When used at lower concentrations (e.g., less than 5 weight percent based on the weight of the oil phase, or about 0.06 weight percent based on the weight of the entire emulsion), these surfactants do not effectively stabilize a HIPE through polymerization to an open-celled foam. See J. M. Williams, D. A. Robleski, *Langmuir*, 4, (1988) 656–662.

Not only does the use of a surfactant add significantly to the cost of HIPE materials, in many applications residual surfactant must be removed from the final product, thus further adding to the cost of producing HIPE materials. For example, as described in U.S. Pat. No. 4,788,225, the surfactant may be an extractable residue which can be removed through post-polymerization rinses. If not removed, the surfactant residue may create a problem when it comes in contact with sensitive human skin.

Therefore, it is desirable to prepare open-celled polymerized HIPE foams with as little extractable surfactant as possible. One way to reduce the amount of extractable surfactant is to use a polymerizable surfactant, as described in U.S. Pat. No. 5,977,194 the contents of which are incorporated herein by reference. Another way is to include a long hydrophobic component which is sufficient to mechanically bind the surfactant into the foam during polymerization.

It would be desirable to provide surfactants which can effectively stabilize HIPEs and form open-celled HIPE materials at relatively low concentrations (e.g., below about 2 weight percent based upon the total weight of the oil phase of the emulsion) and/or which produce HIPE materials with relatively small amounts of extractable surfactants.

SUMMARY OF THE INVENTION

The present invention is a HIPE having at least 70 volume percent of an internal aqueous phase and less than 30 volume percent of an external oil phase wherein the oil phase comprises a polymerizable monomer and a HIPE stabilizing surfactant. Preferably the polymerized HIPE material has a relatively small amount of extractable surfactant (e.g., less than about 5 weight percent and preferably less than about 2 weight percent based upon the weight of the polymer). In one embodiment, the oil phase of the subject HIPE includes less than about 2 weight percent of a highly efficient oil soluble surfactant effective to stabilize the emulsion. In yet another embodiment the invention includes a class of oil soluble, polyoxyalkyl-containing surfactants. Processes for making the subject HIPEs with such surfactants, porous polymeric HIPE materials (e.g., open celled foams) and absorbent articles (e.g., acoustical modulating articles, thermal insulating articles, garments and garment components such as diapers, and/or a filtering article), made from such HIPEs and methods for making such polymeric materials are also part of the present invention.

DETAILED DESCRIPTION OF THE INVENTION

The HIPEs of the present invention are useful in preparing low density polymeric foam materials. Highly hydrophilic foam materials made according to the present invention have a particularly useful application in the manufacture of diapers or other articles which absorb or retain aqueous body fluids.

The high internal phase emulsion (HIPE) of the present invention is a water-in-oil emulsion having greater than about 70 volume percent, more preferably greater than about 90 volume percent and, most preferably greater than about 95 volume percent of an internal aqueous phase and less than about 30 volume percent, more preferably, less than about 10 volume percent and, most preferably, less than about 5 volume percent of an external oil phase. HIPEs of as much as 98 volume percent or more of internal aqueous phase can be made by the present invention. The external oil phase comprises one or more vinyl polymerizable monomers and a cross-linking monomer. The internal aqueous phase comprises water. Typically, a water-soluble radical initiator is added in the aqueous phase. If an oil-soluble initiator is employed, it is added in the oil phase. Additionally, the HIPE comprises a HIPE stabilizing surfactant.

Vinyl polymerizable monomers which can be employed in the practice of the present invention are any polymerizable monomer having an ethylenic unsaturation. In general, the HIPEs are advantageously prepared from either or both (i) at least one monomer that tends to impart glass-like properties (glassy monomers) to the resulting porous polymeric material and (ii) at least one monomer that tends to impart rubber-like properties (rubbery monomers) to the resulting porous polymeric materials.

The glassy monomers are, for the purposes of the present invention, defined as monomeric materials which would produce homopolymers having a glass transition temperature above about 40° C. Preferred glassy monomers include methacrylate-based monomers, such as, for example, methyl methacrylate, and styrene-based monomers, such as, for example, various monovinylidene aromatics such as styrene, o-methylstyrene, chloromethylstyrene, vinylethylbenzene and vinyl toluene. More preferred glassy monomers include styrene, o-methylstyrene, and chloromethylstyrene. The most preferred glassy monomer is styrene.

The rubbery monomers are, for the purposes of the present invention, defined as monomeric materials which would produce homopolymers having a glass transition temperature of about 40° C. or lower. Preferred rubbery monomers include alkyl esters of ethylenically unsaturated acids ("acrylate esters" or "methacrylate esters"), such as 2-ethylhexyl acrylate, butyl acrylate, hexyl acrylate, butyl methacrylate, lauryl methacrylate, isodecyl methacrylate and mixtures thereof; vinyl aliphatic and alicyclic hydrocarbons such as butadiene; isoprene; and combinations of these comonomers. More preferred rubbery monomers include butyl acrylate, 2-ethylhexyl acrylate, butadiene, isoprene and combinations of these comonomers. The most preferred rubbery monomer is 2-ethylhexyl acrylate.

Preferably, the HIPE emulsion includes at least one glassy monomer and at least one rubbery monomer. Without being bound by theory, it is believed that the rubbery monomer provides the foams with flexibility and is used in an amount sufficient to allow compression, bending and twisting during processing, packaging, shipping, storing and use of articles containing such foams, as well as to allow the foam to remain thin until it absorbs liquid, if desired. It is believed the glassy monomer provides the foams with structural integrity and is used in an amount sufficient to minimize the incidence of foam tearing or fragmenting encountered when such foams are subjected to both dynamic and static forces such as, for example, when the wearer of a diaper containing the foam walks, runs, crawls or jumps. The ratio of the glassy monomer to the rubbery monomer generally ranges from 1:25 to 25:1, more preferably from 1:9 to 1.5:1.

While the amount of the vinyl polymerizable monomers most advantageously employed depends on a variety of factors, such as the specific monomers, in general, the vinyl polymerizable monomer is used in an amount of from 50 to 100 weight percent, preferably from 80 to 95 weight percent, and most preferably from 85 to 93 weight percent, based on the total oil phase.

Cross-linking monomers which can be employed in the practice of the present invention for preparing the HIPE include any multifunctional unsaturated monomers capable of reacting with the vinyl monomers. Multifunctional unsaturated cross-linking monomers include, for example, divinylbenzene, ethylene glycol dimethacrylate, 3-butylene dimethacrylate, trimethylolpropane triacrylate and allyl methacrylate. While the amount of cross-linking monomers most advantageously employed depends on a variety of factors, such as the desired polymer modulus, in general, the cross-linking monomer is used in an amount of from 0 to 50 weight percent, preferably from 5 to 20 weight percent, and most preferably from 7 to 15 weight percent, based on the total oil phase.

Radical initiators which can be employed in the practice of the present invention for preparing the HIPE include the water-soluble initiators such as, for example, potassium or sodium persulfate and various redox systems such as ammonium persulfate together with sodium metabisulfite and oil-soluble initiators, such as, for example, azobisisobutyronitrile (AIBN), benzoyl peroxide, methyl ethyl ketone peroxide and di-2-ethyl-hexyl-peroxydicarbonate and lauroyl peroxide. The initiator can be added to the aqueous phase or to the oil phase, depending on whether the initiator is water-soluble or oil-soluble. The initiator should be present in an effective amount to polymerize the monomers. Typically, the initiator can be present in an amount of from 0.005 to 20 weight percent, preferably from 0.1 to 10 weight percent and most preferably from 0.1 to 5 weight percent, based on the total oil phase.

The internal aqueous phase can include a water-soluble electrolyte for aiding the surfactant in forming a stable emulsion, controlling porosity of the foam and/or enhancing the hydrophilicity of the resulting polymeric foam material if left as a residual component of the foam material. Water-soluble electrolytes which can be employed in the practice of the present invention include inorganic salts (monovalent, divalent, trivalent or mixtures thereof), for example, alkali metal salts, alkaline earth metal salts and heavy metal salts such as halides, sulfates, carbonates, phosphates and mixtures thereof. Such electrolytes include, for example, sodium chloride, sodium sulfate, potassium chloride, potassium sulfate, lithium chloride, magnesium chloride, calcium chloride, magnesium sulfate, aluminum chloride and mixtures thereof. Mono- or divalent salts with monovalent anions, such as halides, are preferred. While the amount of electrolytes most advantageously employed depends on a variety of factors, such as the specific compound, the desired porosity of the foam and the surfactant employed, in general, the electrolytes can be employed up to about 20, more preferably up to about 5 and most preferably up to about 1 weight percent, based on the total aqueous mixture.

The internal aqueous phase can additionally comprise a non-electrolyte component, such as, for example, glycerin, as long as a HIPE can still be prepared and polymerized into a foam.

In one embodiment, the surfactants of the present invention are effective at stabilizing HIPEs and producing HIPE materials (e.g. foams) with relative small amounts of extractable surfactants. The term "relatively small amounts of extractable surfactants" means that less than about 5 percent by weight, preferably less than about 2 percent by weight, more preferably less than about 1 percent by weight and most preferably less than about 0.5 percent by weight surfactant, based on the weight of the polymer, can be extracted from the foam (prior to any post-polymerization processing) using simple rinses with water or preferably typical solvents for the surfactants, such as, for example, methanol or isopropanol. The surfactants of the present invention are oil soluble and may be polymerizable or mechanically bound within the polymerized HIPE material, thereby resulting in relatively small amounts of extractable surfactant.

In another embodiment of the invention, the subject surfactants are effective at stabilizing high internal phase emulsions at concentrations at or below about 2 weight percent based upon the total weight of the external oil phase, (and more preferably at less than about 1 percent by weight and most preferably less than about 0.5 weight percent).

It is believed that the highly efficient nature of the subject surfactants is at least partially due to the overall molecular weight and the molecular weight ratio of the hydrophilic and hydrophobic components. Preferably, the molecular weight of the subject surfactants is greater than about 1000, and more preferably from about 1500 to about 8000.

A particularly preferred class of the subject surfactants is an oxyalkylene compound represented by the formula: R[O-(AO)$_m$(CH$_2$CH$_2$O)$_n$R']$_L$ wherein:

R is selected from: C$_1$–C$_{30}$ (preferably C$_2$–C$_{10}$) alkylene, C$_1$–C$_{30}$ (preferably C$_2$–C$_{10}$) alkyl, aryl, and benzyl, wherein the aryl and benzyl may be substituted with at least one of: C$_1$–C$_{30}$ alkylene and C$_1$–C$_{30}$ alkyl. The selection of alkylene, or alkylene substituted aryl or benzyl groups creates a polymerizable group, thereby rendering the surfactant "polymerizable". Preferably such polymerizable groups do not comprise alpha-beta unsaturation. Aryl is a preferred group, however when R is an aryl substituted with an alkylene, preferably the totality of alkylene and alkyl substituents comprise less than 9 carbon atoms, and more preferably less than 4.

A is the same or different and selected from: ethylene and ethylene substituted with C$_1$–C$_{16}$ alkyl. Preferably A is ethylene substituted with a C$_1$–C$_6$ alkyl and more preferably a C$_2$–C$_4$ alkyl.

R' is the same or different and is selected from cationic functionalities such as quaternary ammonium; anionic functionalities such as sulfate, carboxylate, acetate, phosphate, and a corresponding salt (including alkali metal salts e.g. salts formed from sodium, potassium, lithium and ammonium), acid and base of the cationic and anionic functionalities, and hydrogen. R' preferably serves as at least a portion of the hydrophilic component of the surfactant and as such, preferably does not include hydrophobic groups, such as long chain alkyl groups, e.g. fatty acids. Moreover, R' preferably does not comprise an acrylic or methacrylic end cap.

L is an integer from 1 to 4 (preferably 1 or 2); m is an integer from 1 to 200 (preferably from 5–100, more preferably 10–50 and most preferably 20–50), and n is an integer from 0 to 200 (preferably from 0–100, more preferably 5–50 and most preferably 5–30).

Preferred surfactants include those wherein (AO)$_m$ is a homopolymer, block or random copolymer of: ethylene oxide, propylene oxide, 1,2-butylene oxide and 1,2-hexylene oxide, and m is from 20 to 50, e.g., wherein (AO)$_m$ and (CH$_2$CH$_2$O)$_n$ collectively form at least one of: an oxybutylene-oxyethylene-oxybutylene block, and an oxybutylene-oxyethylene block. Further specific examples include surfactants represented by the following formulae:

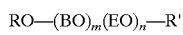

RO—(BO)$_m$(EO)$_n$—R'

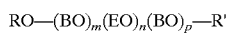

RO—(BO)$_m$(EO)$_n$(BO)$_p$—R' wherein (BO)$_m$ and (BO)$_p$ are polyoxybutylene blocks of "m" and "p"; (EO)$_n$ is a polyoxyethylene block of "n" ethylene oxide units; R, R', m and n are as previously defined, and p is a non-negative integer from 1 to 100. Preferably R' is hydrogen or sulfate. Still more preferred surfactants which can be employed in the practice of the present invention for preparing HIPEs are those represented by the formula:

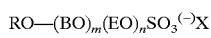

RO—(BO)$_m$(EO)$_n$SO$_3^{(-)}$X wherein R, (BO)$_m$, and (EO)$_n$ are defined previously and X is a counter ion;.

Specific examples of surfactants which can be employed in the practice of the present invention for preparing the water-in-oil HIPEs are those represented by any one of the following formulae:

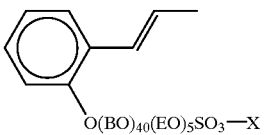

O(BO)$_{40}$(EO)$_5$SO$_3$—X

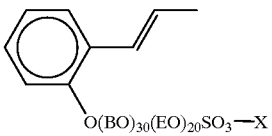

O(BO)$_{30}$(EO)$_{20}$SO$_3$—X

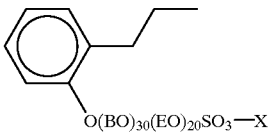

O(BO)$_{30}$(EO)$_{20}$SO$_3$—X or

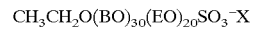

CH$_3$CH$_2$O(BO)$_{30}$(EO)$_{20}$SO$_3^-$X wherein X is pyridinium, ammonium, or a mixture of both.

Generally, the nonionic polyoxybutylene-polyoxyethylene-based surfactants can be prepared by the standard anionic polymerization of monoepoxides, such as, for example, ethylene oxide and butylene oxide, using either a monohydroxyfunctional or dihydroxy functional initiator compound and a catalytic amount of a base, as described in "Polymer Syntheses (I)" *Organic Chemistry Series* Volume I, Stanley R. Sandler, Wolf Karo, 1974, pp. 184–189. Polyether sulfates can be prepared through sulfation of the corresponding polyether alcohol using sulfamic acid as described in "Organic Functional Group Preparations"; *Organic Chemistry Series*, Volume 12-III, Second Ed., Stanley R. Sandler, Wolf Karo, 1989, pp. 148–149. Preparations of the aforementioned compounds are described in detail in the examples.

It has been observed that some of the sulfate-based surfactants tended to lose their efficiency, that is, more surfactant is required to form a HIPE, over time. Although not intended to be bound by theory, it is believed that the sulfate is gradually cleaved over time through a hydrolysis process, producing an alcohol-terminated surfactant. Since sulfates are known to be hydrolytically unstable at a pH below 6 and at a pH above 10, such a hydrolysis can be controlled by controlling the pH of the surfactant.

For most of the surfactants tested, the sulfonated form of the surfactant (sulfate-terminated surfactant) has been found to be more efficient than the corresponding alcohol form (alcohol-terminated surfactant) represented, for example, by the formula:

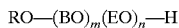

RO—(BO)$_m$(EO)$_n$—H

However, some of the alcohol-terminated surfactants have been found to be nearly as efficient as the corresponding sulfate-terminated surfactants, such as when m and n in the above formula are 30 and 50, respectively, as demonstrated in Examples 14 to 21. These alcohol-terminated surfactants have also been found to demonstrate high efficiency in forming polymerized HIPE foams.

The amount of surfactant used must be such that a water-in-oil high internal phase emulsion will form. Generally, the amount of surfactant needed varies with the specific surfactant and the type of formulation used. As little as about 0.125 weight percent, or less, based on oil phase can be used. More generally, as little as about 0.25 weight percent based on oil phase can be used. Generally, up to about 25 weight percent or more, based on the oil phase, can be used if desired.

Methods for preparing water-in-oil emulsions are known in the art such as, for example, in U.S. Pat. 4,522,953 and 5,210,104, and these methods can be employed in the practice of the present invention. For example, the water-in-oil HIPE can be prepared in batches. In general, to form a water-in-oil HIPE in batch quantities, the water phase is gradually added to a mixture of oil phase and surfactant while the mixture is being agitated. Agitation can be accomplished any number of ways including impeller-type agitation. Alternatively, water-in-oil HIPEs can be prepared in a continuous flow manner. Methods for continuous flow HIPE preparation are also well established in the literature. See, for example, U.S. Pat. Nos. 4,018,426 and 5,198,472.

The following working examples are given to illustrate the invention and should not be construed to limit its scope. Unless otherwise indicated, all parts and percentages are by weight.

EXAMPLE 1

Preparation of 1-Butylene Oxide (40) Ethylene Oxide (5) 3-Propenylphenyl Pyridinium Sulfate (Surfactant 1)

The potassium salt of 2-allylphenol was formed from a 1:1 molar mixture of potassium ethoxide and 2-allylphenol whereby the ethanol formed during the reaction was removed under high vacuum. Sequential alkoxylation of 1,2-butylene oxide (approximately 40 units per molecule) and ethylene oxide (approximately, an average of 5 units per molecule) was conducted utilizing the potassium salt of 2-allylphenol as initiator/catalyst in toluene at 120° C. in a Parr reactor. During the course of the polymerization, the allylphenyl moiety undergoes base-catalyzed isomerization to the corresponding 2-propenylphenoxy compound. The resulting diblock copolymer was neutralized with dilute HCl, filtered and the volatiles were removed by roto-evaporation. The diblock-copolymer was characterized by GPC and NMR. This 2-propenyl-phenoxypoly BO/EO-monol was heated in the presence of sulfamic acid and pyridine to form the corresponding pyridinium sulfate. This material was heated at 60° C. under high vacuum to remove residual pyridine and other volatile components. The degree of sulfamation was determined by 1H NMR spectroscopy

EXAMPLE 2

Open-celled Polymerized HIPE Foam Using 0.25 Weight Percent Surfactant 1 Based on the Monomer Phase (0.0125 Weight Percent Based on Entire Emulsion)

Into a monomer phase composed of 4.79 g 2-ethylhexyl acrylate, 1.05 g styrene, 1.64 g divinylbenzene (55 percent active) and 0.10 g lauroyl peroxide initiator was dissolved 0.0188 g of the surfactant from example 1. The components form a clear solution. An aqueous phase was prepared by dissolving 1.42 g calcium chloride dihydrate and 0.17 g potassium persulfate into 141.08 g deionized water. This aqueous phase was added dropwise to the monomer/ surfactant solution while mixing in a 250-mL beaker using a 3-paddle agitator at 300 RPM. The resulting HIPE was placed into a dish covered with SARAN™ WRAP and put in a forced-air oven at 65° C. for 15 hours. A water saturated polymeric foam was obtained. The water phase can be squeezed out without fracturing the foam by compressing, indicating an open-celled structure.

EXAMPLE 3

Preparation of 1-Polybutyleneoxide(30)-Polyethyleneoxide(20) 3-Propenyl-phenyl Pyridinium Sulfate (Surfactant 2)

Another surfactant was prepared as described in Example 1 except the number of 1,2-butylene oxide units per molecule was approximately 30 and the number of ethylene oxide units per molecule was approximately 20.

EXAMPLE 4

Open-celled Polymerized HIPE Foam using 0.25 Weight Percent Surfactant 2 Based on Monomer Phase (0.0125 Weight Percent Based on Entire Emulsion)

A HIPE was prepared and polymerized as described in Example 2 except Surfactant 2 was used instead of Surfactant 1.

EXAMPLE 5

Preparation of 1-Polybutyleneoxide(30)-Polyethyleneoxide(20) 3-Propyl-phenyl Pyridinium Sulfate (Surfactant 3)

Another surfactant was prepared as described in Example 3 except the sodium salt of 2-propylphenol was used as the initiator/catalyst instead of the sodium salt of 2-allylphenol.

EXAMPLE 6

Open-Celled Polymerized HIPE Foam Using 0.12 Weight Percent Surfactant 3 Based on the Monomer Phase (0.006 Weight Percent Based on Entire Emulsion)

A polymerized HIPE foam was prepared as described in Example 4 except 0.0095 g of Surfactant 3 was used instead of 0.0188 g of Surfactant 2.

The resulting foam was soaked in isopropanol for 2 days and then squeezed free of the internal aqueous phase. The foam was open-celled, as determined by Scanning Electron Microscopy (SEM).

EXAMPLE 7

Preparation of Polybutyleneoxide(30)-Polyethyleneoxide(20) Pyridinium Sulfate (Surfactant 4)

Sequential alkoxylation of 1,2-butylene oxide (approximately 30 units per molecule) and ethylene oxide (approximately 20 units per molecule) was conducted using potassium ethoxide as initiator/catalyst in toluene at 120° C. in a Parr reactor. The resulting diblock copolymer was neutralized with dilute HCl, filtered, and the volatiles were removed by roto-evaporation. The diblock-copolymer was characterized by GPC and NMR. This polyBO/EO-monol was heated in the presence of sulfamic acid and pyridine to form the corresponding pyridinium sulfate. This material was heated at 60° C. under high vacuum to remove residual pyridine and other volatile components. The degree of sulfamation was determined by $^1$H NMR spectroscopy.

EXAMPLE 8

Open-Celled Polymerized HIPE Foam Using 0.25 weight Percent Surfactant 4 Based on the Monomer Phase (0.0125 Weight Percent Based on Entire Emulsion)

A HIPE was prepared and polymerized as described in Example 2, except Surfactant 4 was used instead of Surfactant 1.

EXAMPLES 9 TO 12 AND COMPARATIVE EXAMPLE A

The efficiency of Surfactants 1 to 4 was evaluated by determining the minimum amount of surfactant required to form a polymerized open-celled HIPE foam from a 95 percent internal phase HIPE. Several HIPE formulations were prepared with surfactant concentrations ranging from 0.125 to 30 weight-percent based on the weight of the monomer phase while maintaining a 95-weight percent internal phase. The internal phase comprises 4.79 g 2-ethylhexyl acrylate, 1.05 g styrene, 1.64 g divinylbenzene and 0.10 g lauroyl peroxide. The external phase comprised 141.08 g deionized water, 1.42 g $CaCl_2 \cdot 2H_2O$ and 0.17 g $K_2S_2O_8$.

The surfactants were generally tested first with the 1-weight percent formulation (based on weight of monomer phase). If the l-weight percent formulation successfully produced a polymerized open-celled HIPE foam, the 0.5-weight percent formulation was tested next, and so on until a HIPE foam could no longer be produced using the emulsification and polymerization methods described in Example 2. If the 1-weight percent recipe failed to produce a polymerized HIPE foam, the 2-weight percent formulation was tested, and so on, until a foam was produced using the emulsification and polymerization methods described in Example 2. For comparative purposes, a known surfactant system (Surfactant A) comprising 75 percent sorbitan monooleate and 25 percent sorbitan trioleate was tested along with Surfactants 1 to 4. Surfactant A was prepared in accordance with the procedure described in Example 1 of U.S. Pat. No. 5,260,345. The test results are summarized in Table II, using the ratings shown in Table I.

TABLE I

| Rating | Description |
| --- | --- |
| 1 | Foam |
| 2 | Polymeric Webbed Network |
| 3 | High Temperature Phase Separation |
| 4 | Temporary Emulsion |
| 5 | No Emulsion |

TABLE II

| Ex. | SURFACTANT | 0.125% | 0.25% | 0.5% | 1 | 2 | 4 | 6 | 8 | 10 | 15 |
| --- | --- | --- | --- | --- | --- | --- | --- | --- | --- | --- | --- |
| 9 | Surfactant 1 | 3 | 1 | 1 | 1 | | | | | | |
| 10 | Surfactant 2 | 3 | 1 | 1 | 1 | | | | | | |
| 11 | Surfactant 3 | 1 | 1 | 1 | 1 | | | | | | |
| 12 | Surfactant 4 | 3 | 1 | 1 | 1 | | | | | | |
| C. Ex | Surfactant A | | | | | 4 | 4 | | 3 | 3 | 1 |

The data in Table II show that the surfactants of the present invention were more efficient in forming HIPE foams compared to the known surfactant. The known surfactant system required 15-weight percent surfactant based on the weight of the monomer phase to form a foam, while the surfactants of the present invention produced a stable HIPE foam at a concentration of as little as 0.125 weight percent surfactant based on the weight of the monomer phase (0.0006 weight percent based on the entire HIPE). Furthermore, foams prepared with the surfactants of the present invention at a concentration of 0.125-weight percent surfactant, based on the monomer phase, were open-celled, as determined by SEM.

EXAMPLE 13

Open-Celled Foam Prepared From an Approximately 99 Percent Internal Phase Emulsion Into a monomer phase composed of 1.30 g 2-ethylhexyl acrylate, 0.28 g styrene, 0.45 g divinylbenzene (55 percent active) and 0.03 g lauroyl peroxide initiator was dissolved 0.22 g freshly prepared Surfactant 3 from Example 5. An aqueous phase was prepared by dissolving 2.42 g calcium chloride dihydrate and 0.28 g potassium persulfate into 239.3 g of deionized water. All but 53 g of the aqueous phase was slowly emulsified into the monomer/surfactant solution using a dropwise addition while agitating at 115 RPM using a 3-paddle mixer. A thick HIPE resulted. The HIPE was placed into a Pyrex™ (trademark of Corning Glass Works) dish and covered with SARAN™ WRAP (The Dow Chemical Co.) and put into a forced-air oven at 65° C. for 21.5 hours. An aqueous filled polymeric foam was produced. The aqueous phase could easily be squeezed from the foam indicating an open-celled foam. Once rinsed with isopropanol, the foam dried to a collapsed state. Upon re-exposure to isopropanol, the clean, dry foam expanded, reabsorbing over 99 mL of isopropanol per gram of dry foam.

EXAMPLES 14 TO 21

Performance of Alcohol-Terminated Surfactant Versus Sulfate-Terminated Surfactant A series of eight surfactants was prepared following a procedure similar to that in Example 7 such that the following block sizes were obtained:

a) BO(30)EO(5); b) BO(30)EO(10); c) BO(30)EO(20); d) BO(30)EO(50)

A portion of each material (a–d) was isolated as the poly(BO/EO)-monol and a portion of each material (a–d) was sulfonated according to the procedure in Example 7. The following eight surfactants were obtained:

| | |
| --- | --- |
| EtO-BO(30)EO(5)-H | EtO-BO(30)EO(5)-$SO_3^{(-)}$X |
| EtO-BO(30)EO(10)-H | EtO-BO(30)EO(10)-$SO_3^{(-)}$X |
| EtO-BO(30)EO(20)-H | EtO-BO(30)EO(20)-$SO_3^{(-)}$X |
| EtO-BO(30)EO(50)-H | EtO-BO(30)EO(50)-$SO_3^{(-)}$X | wherein X was either a pyridinium, ammonium, or a combination of both.

The efficiency of these eight surfactants was evaluated following the procedure in Examples 9 to 12. The results are summarized in Table III, using the ratings shown in Table I.

TABLE III

| Ex. | Surfactant | 0.125% | 0.25% | 0.5% | 1% | 8% | 10 | 20 |
|---|---|---|---|---|---|---|---|---|
| 14 | EtO-BO(30)EO(5)-H | | | | | | 4 | 4 |
| 15 | EtO-BO(30)EO(5)-SO$_3^{(-)}$X | 1 | 1 | 1 | 1 | | | |
| 16 | EtO-BO(30)EO(10)-H | | | | | 4 | 4 | |
| 17 | EtO-BO(30)EO(10)-SO$_3^{(-)}$X | | 3 | 1 | 1 | | | |
| 18 | EtO-BO(30)EO(20)-H | | | 3 | 1 | | | |
| 19 | EtO-BO(30)EO(20)-SO$_3^{(-)}$X | 3 | 1 | 1 | 1 | | | |
| 20 | EtO-BO(30)EO(50)-H | | | 4 | 1 | | | |
| 21 | EtO-BO(30)EO(50)-SO$_3^{(-)}$X | | | 5 | 1 | | | |

EXAMPLE 22

HIPE Foam Prepared without Salt in the Aqueous Phase

Into a monomer phase composed of 1.73 g 2-ethylhexyl acrylate, 0.38 g styrene, 0.59 g divinylbenzene (55 percent active) and 0.1 g lauroyl peroxide initiator was dissolved 0.30 g freshly prepared Surfactant 2 from Example 3. To this mixture was slowly added 147.0 g water while stirring at 300 RPM using a 3-paddle mixer. The resulting high internal phase emulsion was poured into Pyrex™ dishes, covered with Saran™ Wrap and cured in a forced-air oven at 65 degrees C for 18 hours. The resulting foam can be squeezed free of aqueous phase.

EXAMPLE 23

High Temperature Cure of HIPE

Into a monomer phase composed of 2.63 g 2-ethylhexyl acrylate, 0.61 g styrene, 0.61 g divinylbenzene (55 percent active) was dissolved 0.04 g lauroyl peroxide and 0.15 g of Surfactant 2 (from Example 3). An aqueous phase was prepared by dissolving 1.96 g calcium chloride dihydrate and 0.33 g potassium persulfate into 194.04 g of water. The aqueous phase was added dropwise to the monomer solution while mixing at 300 RPM with a 3-paddle mixer. The emulsion was mixed an additional 2 minutes after all of the water was added to ensure homogeneity. The resulting high internal phase emulsion was placed into Pyrex™ dishes, covered with Saran™ Wrap, and placed in a forced-air oven at 95° C. for 19.5 hours (overnight) to cure. The resulting foam can be squeezed free of the aqueous phase.

What is claimed is:

1. A surfactant represented by the formula:

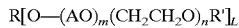

$$R[O-(AO)_m(CH_2CH_2O)_nR']_L$$

wherein:

R contains no polymerizable functional groups and is selected from: $C_1$–$C_{30}$ alkyl, aryl, and benzyl, wherein the aryl and benzyl may be substituted with $C_1$–$C_{30}$ alkyl;

A is the same or different and selected from: ethylene and ethylene substituted with $C_1$–$C_{16}$ alkyl;

R' is the same or different and is selected from: quaternary ammonium, sulfate, carboxylate, acetate, phosphate, and a corresponding salt, acid and base thereof, and hydrogen;

L is an integer from 1 to 4; m is an integer from 1 to 200, and n is an integer from 0 to 200.

2. The surfactant of claim 1 wherein R' is selected from at least one of quaternary ammonium and sulfate, a corresponding salt, acid and base thereof.

3. The surfactant of claim 1 wherein $(AO)_m$ is a homopolymer, block or random copolymer of: ethylene oxide, propylene oxide, 1,2-butylene oxide and 1,2-hexylene oxide.

4. The surfactant of claim 1 wherein m is from 20 to 50 and (AO) is a homopolymer of 1,2-butylene oxide.

5. The surfactant of claim 1 wherein m is from 20 to 50 and (AO) is a copolymer of 1,2-butylene oxide and 1,2-hexylene oxide.

6. The surfactant of claim 1 where $(AO)_m$ and $(CH_2CH_2O)_n$ collectively form at least one of: an oxybutylene-oxyethylene-oxybutylene block and an oxybutylene-oxyethylene block.

7. The surfactant of claim 1 wherein L is 1, and m and n are from 5 to 50.

8. The surfactant of claim 1 having a molecular weight of greater than 1000.

9. The surfactant of claim 8 having a molecular weight of from about 1500 to 8000.

* * * * *